United States Patent [19]

Cotrel et al.

[11] B 4,001,271
[45] Jan. 4, 1977

[54] 3-(ISOPROPYL AMINO ALKOXY)-2-PHENYL-ISOINDOLIN-1-ONES

[75] Inventors: Claude Cotrel, Paris; Claude Jeanmart, Brunoy; Mayer Naoum Messer, Bievres, all of France

[73] Assignee: Rhone-Poulenc, S.A., Paris, France

[22] Filed: Feb. 7, 1974

[21] Appl. No.: 440,548

[44] Published under the second Trial Voluntary Protest Program on March 16, 1976 as document No. B 440,548.

[30] Foreign Application Priority Data

Feb. 8, 1973 France .............. 73.04460

[52] U.S. Cl. .............. 260/325 PH; 260/295 B; 260/294.9; 424/274

[51] Int. Cl.$^2$ ...................... C07D 209/46

[58] Field of Search .............. 260/325 PH

[56] References Cited

UNITED STATES PATENTS 3,818,011  6/1971  Challier et al. .............. 260/325 PH 3,898,232  8/1975  Cotrel et al. .............. 260/325 PH

OTHER PUBLICATIONS

Usov et al., "Chem. Abstracts," vol. 72, p. 370, No. 90230p, (1970).

*Primary Examiner*—Lewis Gotts
*Assistant Examiner*—S. P. Williams
*Attorney, Agent, or Firm*—Stevens, Davis, Miller & Mosher

[57] ABSTRACT

Isoindolin-1-one derivatives carrying on the nitrogen atom in the 2-position a phenyl or pyridyl radical, optionally carrying one or two substituents selected from halogen, alkyl ($C_1$–$C_4$), alkoxy ($C_1$–$C_4$), cyano and trifluoromethyl, and in the 3-position a grouping —O—T—$NR_1R_2$ wherein T is alkylene ($C_2$–$C_6$), and $R_1$ and $R_2$ represent hydrogen or alkyl ($C_1$–$C_4$), are new compounds possessing pharmacodynamic properties and are useful as anti-arrhythmic agents.

6 Claims, No Drawings

3-(ISOPROPYL AMINO ALKOXY)-2-PHENYL-ISOINDOLIN-1-ONES

This invention relates to new therapeutically useful isoindoline derivatives, processes for their preparation and pharmaceutical compositions containing them.

The new isoindoline derivatives of the present invention are those of the general formula:

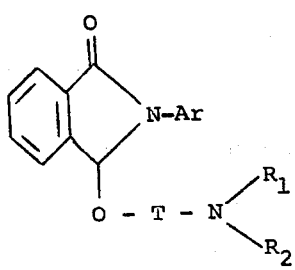

wherein Ar represents a phenyl radical or a pyridyl (preferably 2-pyridyl) radical optionally carrying one or two substituents, which — in the latter case — may be identical or different, selected from halogen (e.g. chlorine) atoms, alkyl radicals containing 1 to 4 carbon atoms (e.g. methyl), alkoxy radicals containing 1 to 4 carbon atoms (e.g. methoxy), the cyano radical and the trifluoromethyl group, T represents a straight or branched alkylene radical containing 2 to 6 carbon atoms, and $R_1$ and $R_2$, which may have the same or different significances, each represent a hydrogen atom or a straight or branched alkyl radical containing 1 to 4 carbon atoms (e.g. methyl, ethyl or isopropyl), and acid addition salts thereof.

According to a feature of the invention, the isoindoline derivatives of general formula I are prepared by the process which comprises reacting an amine of the general formula:

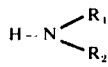

(wherein $R_1$ and $R_2$ are as hereinbefore defined) with an isoindoline derivative of the general formula:

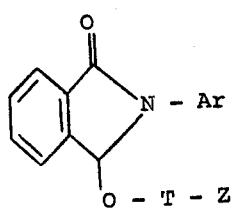

wherein Ar and T are as hereinbefore defined, and Z represents the acid residue of a reactive ester such as a halogen (preferably chlorine) atom or a sulphuric or sulphonic ester radical, e.g. methoxysulphonyloxy, methanesulphonyloxy or p-toluenesulphonyloxy. The reaction is generally carried out in the presence or absence of an inert organic solvent, for example toluene, at a temperature between 80° and 150°C. The reaction is preferably effected without a solvent, working in an autoclave.

The compounds of general formula III can be obtained by reacting a compound of the general formula:

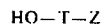

(wherein T and Z are as hereinbefore defined) with an isoindoline derivative of the general formula:

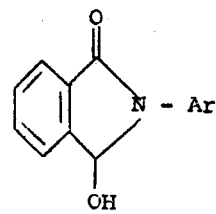

wherein Ar is as hereinbefore defined. The reaction is generally carried out in an inert organic solvent, for example toluene, in the presence of an acid such as p-toluenesulphonic acid, and the water formed is removed by azeotropic distillation.

The isoindoline derivatives of general formula V can be obtained by reducing a phthalimide of the general formula:

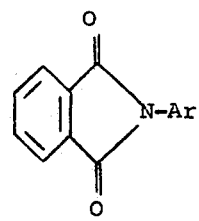

(wherein Ar is as hereinbefore defined) by methods known per se for reducing one of the carbonyl groups of a phthalimide to a >CH—OH group. The reduction is generally carried out by means of magnesium in a mixture of methanol and a saturated solution of ammonium chloride, or by means of an alkali metal borohydride in an aqueous or aqueous-alcoholic medium.

The phthalimides of general formula VI can be obtained by reacting an amine of the general formula:

(wherein Ar is as hereinbefore defined) with o-phthalic acid anhydride.

According to another feature of the invention, the isoindoline derivatives of general formula I are prepared by the process which comprises reacting an amino compound of the general formula:

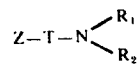

(wherein T, $R_1$, $R_2$ and Z are as hereinbefore defined) with an alkali metal salt, optionally prepared in situ, of an isoindoline derivative of general formual V, wherein Ar is as hereinbefore defined. The reaction is generally carried out in an inert anhydrous organic solvent, for example dimethylformamide, at a temperature between 20° and 80°C.

The isoindoline derivatives of general formula I obtained by the aforementioned processes can be purified by physical methods such as distillation, crystallisation or chromatography, or by chemical methods such as formation of salts, crystallisation of the salts and decomposition of them in an alkaline medium. In carrying out the said chemical methods the nature of the anion of the salt is immaterial, the only requirement being that the salt must be well defined and readily crystallisable.

The isoindoline derivatives of general formula I may be converted by methods known per se into acid addition salts. The acid addition salts can be obtained by the action of acids in appropriate solvents. As organic solvents there may be used alcohols, ketones, ethers or chlorinated hydrocarbons. The salt which is formed is precipitated, if necessary after concentration of the solution, and is isolated by filtration or decantation.

By the term "methods known per se" as used in this specification is meant methods hereinbefore used or described in the chemical literature.

The isoindoline derivatives of the invention and their addition salts possess valuable pharmacodynamic properties; they are very active as anti-arrhythmic agents. In vitro, at concentrations of between 1 and 10 mg./liter, they have proved to be active in an investigation of the prolongation of the refractory period of auricles isolated from rabbits [G. S. Dawes, Brit. J. Pharmacol., 1, 90 (1946)]. In vivo, they have proved to be active in rabbits against cardiographic anomalies caused by aconitine and in dogs against ventricular tachyarrhythmia caused by ouabain [B. R. Lucchesi et al, J. Pharmacol., 132, 372 (1961) and Ann. N. Y. Acad. Sc., 139, art. 3, 940 (1967)]at doses between 0.1 and 10 mg./kg. animal body weight when administered intravenously. Moreover, they show low toxicity; when administered orally to mice the $LD_{50}$ is between 50 and 1,000 mg./kg. animal body weight; when administered intravenously to the same animal the $LD_{50}$ is between 10 and 100 mg./kg. animal body weight.

Of outstanding importance are those isoindoline derivatives of general formula I in whch Ar represents an unsubstituted phenyl or 2-pyridyl radical, and more particularly those in which Ar represents the phenyl radical, $R_1$ represents a hydrogen atom and $R_2$ represents the isopropyl radical, for example 3-(2-isopropylaminoethoxy)-2-phenyl-isoindolin-1-one, 3-(4-isopropylaminobutoxy)-2-phenyl-isolindolin-1-one, 3-(5-isopropylaminopentyloxy)-2-phenyl-isoindolin-1-one, 3-(3-isopropylaminopropoxy)-2-phenyl-isoindolin-1-one, and 3-(3-isopropylamino-2-methylpropoxy)-2-phenyl-isoindolin-1-one.

For therapeutic purposes, the isoindoline derivatives of general formula I may be employed as such or in the form of non-toxic salts, i.e. salts containing anions which are relatively innocuous to the animal organism in therapeutic doses of the salts, (such as hydrochlorides, sulphates, nitrates, phosphates, acetates, propionates, succinates, benzoates, fumarates, maleates, tartrates, theophyllinacetates, salicylates, phenolphthalinates and methylene-bis-β-hydroxynaphthoates) so that the beneficial physiological properties in the basis are not vitiated by side effects ascribable to the anion.

The following non-limitative Examples illustrate the invention.

EXAMPLE 1

A solution of 3-(2-chloroethoxy)-2-phenyl-isoindolin-1-one in isopropylamine (120cc.) is heated in an autoclave at 120°C. for 24 hours. After cooling, the reaction mixture is poured into water (200 cc.) and 4N sodium hydroxide solution (16 cc.). The alkaline solution obtained is extracted with diethyl ether (250 cc.). The organic solution is washed with water (3 × 50 cc.) and is then extracted with 4N hydrochloric acid (18 cc.). The acid solution obtained is rendered alkaline by adding 4N sodium hydroxide solution (20 cc.) and the oily product which separates out is extracted with diethyl ether (2 × 100 cc.). The organic extracts are then dried over sodium sulphate and concentrated to dryness under reduced pressure. A product (14.2 g.), which melts at about 85°C., is obtained and is dissolved in acetone (150 cc.). A 4.03N solution of hydrogen chloride in diethyl ether (11.3 cc.) is added to the resulting solution. The product which crystallises is filtered off and then washed with acetone (10 cc.). After drying, 3-(2-isopropylaminoethoxy)-2-phenyl-isoindolin-1-one hydrochloride (11.3 g.), which melts at 184°C., is obtained.

3-(2-Chloroethoxy)-2-phenyl-isoindolin-1-one can be obtained by refluxing a solution of 3-hydroxy-2-phenyl-isoindolin-1-one (22.5 g.) and glycol monochlorohydrin (7.7 g.) in anhydrous toluene (200 cc.) in the presence of p-toluenesulphonic acid (0.5 g.) in a Dean-Stark apparatus. Heating is continued until all the water formed has been entrained azeotropically. The cooled reaction mixture is then washed with 2N sodium hydroxide solution (50 cc.) and then with water (2 × 50 cc.). The organic solution obtained is dried over sodium sulphate and concentrated to dryness under reduced pressure. The residue obtained is taken up in diisopropyl ether (50 cc.) and the insoluble product is filtered off and washed with diisopropyl ether (6 cc.). After drying, 3-(2-chloroethoxy)-2-phenyl-isoindolin-1-one (20.1 g.), which melts at 71°C., is obtained.

EXAMPLE 2

Following the procedure of Example 1 but starting with 3-(4-chlorobutoxy)-2-phenyl-isoindolin-1-one (18.9 g.) and isopropylamine (51 cc.), 3-(4-isopropylaminobutoxy)-2-phenyl-isoindolin-1-one hydrochloride (16.8 g.), which melts at 158°C., is obtained.

3-(4-Chlorobutoxy)-2-phenyl-isoindolin-1-one, which melts at 86°C., can be prepared by the procedure described in Example 1 from 3-hydroxy-2-phenyl-isoindolin-1-one (22.5 g.), p-toluenesulphonic acid (0.5 g.) and 4-chlorobutan-1-ol (11.9 g.).

EXAMPLE 3

A solution of 3-(5-chloropentyloxy)-2-phenyl-isoindolin-1-one (31.6 g.) and isopropylamine (83 cc.) in toluene (50 cc.) is heated in an autoclave at 140°C. for 48 hours. After cooling, the reaction mixture is poured into water (200 cc.) and diethyl ether (200 cc.). The organic phase is separated. The aqueous solution is washed with diethyl ether (2 × 55 cc.). The organic solutions obtained are combined and washed with water (5 × 25 cc.) and are then extracted with 4N hydrochloric acid (3 × 35 cc.). The acid solutions obtained are combined and rendered alkaline by adding 10N sodium hydroxide solution (45 cc.). The resulting insoluble oil is extracted with methylene chloride (3 × 80 cc.) and the organic solution obtained is dried over sodium sulphate and concentrated to dryness under reduced pressure. An oil (30 g.) is obtained and is dissolved in isopropanol (250 cc.). Fumaric acid (9.3 g.) is added to the solution and the mixture is then heated to the boiling point. A slight amount of insoluble matter is removed by carrying out a hot filtration. The product which crystallises on cooling is filtered off and then washed with isopropanol (50 cc.) and acetone (50 cc.). After drying, 3-(5-isopropyl-aminopentyloxy)-2-phenyl-isoindolin-1-one hydrogen fumarate (30.6 g.), which melts at 150°C., is obtained.

3-(5-Chloropentyloxy)-b 2-phenyl-isoindolin-1-one, in the form of a yellow oil, can be prepared by the procedure described in Example 1 from 3-hydroxy-2-phenyl-isoindolin-1-one (22.5 g.), p-toluenesulphonic acid (0.5 g.) and 5-chloropentan-1-ol (13.5 g.).

EXAMPLE 4

Following the procedure of Example 1 but starting with 3-(3-chloropropoxy)-2-phenyl-isoindolin-1-one (5.9 g.) and isopropylamine (40 cc.), 3-(3-isopropylaminopropoxy)-2-phenyl-isoindolin-1-one hydrochloride (5.05 g.), which melts at 178°C., is obtained.

3-(3-Chloropropoxy)-2-phenyl-isoindolin-1-one, which melts at 96°C., can be prepared by the procedure described in Example 1 from 3-hydroxy-2-phenyl-isoindolin-1-one (22.5 g.), p-toluenesulphonic acid (0.5 g.) and 3-chloropropan-1-ol (10.4 g.).

EXAMPLE 5

A solution of 3-(3-chloro-2-methylpropoxy)-2-phenyl-isoindolin-1-one (24.7 g.) in isopropylamine (250 cc.) is heated in an autoclave at 120°C. for 24 hours. After cooling, the reaction mixture is concentrated to dryness under reduced pressure and the residue is then taken up in a 5N aqueous solution of sodium hydroxide (30 cc.), water (200 cc.) and diethyl ether (200 cc.). The ether solution is washed three times with distilled water (total 150 cc.) and is extracted four times with a 2N aqueous solution of methanesulphonic acid (total 200 cc.). The acid solution is washed three times with diethyl ether (total 150 cc.) and is then rendered alkaline by adding 10N sodium hydroxide solution (50 cc.). The oil which separates out is extracted four times with diethyl ether (total 200 cc.). The organic extracts are combined, washed five times with distilled water (total 250 cc.), dried over anhydrous magnesium sulphate and concentrated to dryness under reduced pressure. The residue obtained (22.2 g.) is dissolved in acetone (130 cc.). A solution of oxalic acid (6.2 g.) in acetone (30 cc.) is added to the solution obtained. After cooling for 3 hours at 2°C., the product which has crystallised is filtered off and washed twice with acetone (total 20 cc.) and then with diethyl ether (30 cc.). After drying, 3-(3-isopropylamino-2-methylpropoxy)-2-phenyl-isoindolin-1-one hydrogen oxalate (26.6 g.), which melts at 150°C., is obtained.

3-(3-Chloro-2-methylpropoxy)-2-phenyl-isoindolin-1-one, in the form of a pale yellow oil, can be prepared by the procedure described in Example 1 from 3-hydroxy-2-phenyl-isoindolin-1-one (22.5 g.), p-toluenesulphonic acid (0.5 g.) and 3-chloro-2-methylpropan-1-ol (12 g.).

3-Chloro-2-methylpropan-1-ol can be prepared in accordance with the method described by A. Bruylants et al, Bull. Soc. Chim. Belg., 61, 366 (1952).

EXAMPLE 6

A solution of 3-hydroxy-2-(2-pyridyl)-isoindolin-1-one (17.85 g.) in anhydrous dimethylformamide (100 cc.) is added to a suspension of sodium hydride (50% dispersion in mineral oil) (3.9 g.) in anhydrous dimethylformamide (40 cc.), the temperature being kept at about 25°C. When the evolution of gas has ceased, 1-chloro-2-diethylaminoethane (11 g.) is added and the reaction mixture is then heated for 2 hours at a temperature of about 50°C. After cooling, the reaction mixture is poured into distilled water (750 cc.) and 4N methanesulphonic acid (50 cc.). The acid solution obtained is washed with chloroform (2 × 100 cc.) and then rendered alkaline by adding 4N sodium hydroxide solution (60 cc.). The oil which separates out is extracted with chloroform (3 × 100 cc.) and the organic solution obtained is then washed with water (50 cc.), dried over sodium sulphate and evaporated to dryness under reduced pressure. The residual oil is dissolved in ethanol (250 cc.); a 7.3N aqueous solution of hydroiodic acid (10 cc.) is added to the solution obtained. The product which crystallises is filtered off and washed with ethanol (25 cc.). After recrystallisation from ethanol, 3-(2-diethylaminoethoxy)-2-(2-pyridyl)-isoindolin-1-one hydroiodide (16.5 g.), which melts at 170°C., is obtained. 3-Hydroxy-2-(2-pyridyl)-isoindolin-1-one can be prepared in accordance with the method which is described in Belgian Pat. No. 771,493.

EXAMPLE 7

Following the procedure of Example 6 but starting with 3-hydroxy-2-(2-pyridyl)-isoindolin-1-one (22.5 g.), sodium hydride (50% dispersion in mineral oil) (4.5 g.) and 1-chloro-3-dimethylaminopropane (12.5g.), 3-(3-dimethylaminopropoxy)-2-(2-pyridyl)-isoindolin-1-one hydroiodide (15.5 g.), which melts at 128°-130°C., is obtained.

EXAMPLE 8

Following the procedure of Example 6 but starting with 3-hydroxy-2-phenyl-isoindolin-1-one (22.5 g.), sodium hydride (50% dispersion in mineral oil) (5.3 g.) and 1-chloro-2-diethylaminoethane (13.5 g.), 3-(2-diethylaminoethoxy)-2-phenyl-isoindolin-1-one (34 g.) is obtained in the form of an 85% pure oil. On treating this oil (28 g.) with fumaric acid (8.5 g.) in ethanol, 3-(2-diethylaminoethoxy)-2-phenyl-isoindolin-1-one hydrogen fumarate (27.6 g.), which melts at 146°-147°C., is obtained.

The present invention includes within its scope pharmaceutical compositions comprising, as active ingredient, at least one isoindoline derivative of general formula I, or a non-toxic acid addition salt thereof, in association with a pharmaceutical carrier or coating. The invention includes especially such preparations made up for oral, parenteral or rectal administration.

Solid compositions for oral administration include tablets, pills, powders and granules. In such solid compositions the active compound is admixed with at least one inert diluent such as sucrose, lactose or starch. The compositions may also comprise, as is normal practice, additional substances other than inert diluents, e.g. lubricating agents, such as magnesium stearate. Liquid compositions for oral administration include pharmaceutically-acceptable emulsions, solutions, suspensions, syrups and elixirs containing inert diluents commonly used in the art, such as water or liquid paraffin. Besides inert diluents such compositions may also comprise adjuvants, such as wetting, emulsifying and suspending agents, and sweetening, flavouring and aromatizing agents. The compositions according to the invention, for oral administration, also include capsules of absorbable material such as gelatin containing the active substance with or without the addition of diluents or excipients.

Preparations according to the invention for parenteral administration include sterile aqueous or non-aqueous solutions, suspensions or emulsions. Examples of non-aqueous solvents or vehicles are propylene glycol, polyethylene glycol, vegetable oils such as olive oil, and injectable organic esters such as ethyl oleate. These compositions may also contain adjuvants such as preserving, wetting, emulsifying and dispersing agents. They may be sterilized by, for example, filtration through a bacteria-retaining filter, by incorporation in the compositions of sterilizing agents, by irradiation, or by heating. They may also be manufactured in the form of sterile solid compositions, which can be dissolved in sterile water or some other sterile injectable medium immediately before use.

Compositions for rectal administration are suppositories which contain, in addition to the active substance, excipients such as cacao butter or a suitable wax base.

The percentage of active ingredient in the compositions of the invention may be varied, it being necessary that it should constitute a proportion such that a suitable dosage shall be obtained. The dosage depends on the desired therapeutic effect, on the route of administration and on the duration of the treatment.

The compositions are particularly useful in the treatment of rhythm disorders and cardiac excitability. In human therapy, the compositions when administered orally to an adult should generally give doses between 50 and 1,000 mg. of active substance per day. In general the physician will decide the posology considered appropriate, taking into account the age, weight and other factors intrinsic to the patient being treated.

The following Example illustrates pharmaceutical compositions according to the invention.

EXAMPLE 9

Tablets containing 25 mg. of active substance and having the following composition are prepared in accordance with the usual technique:

| | |
|---|---|
| 3-(3-isopropylaminopropoxy)-2-phenyl-isoindolin-1-one hydrochloride | 0.029 g. |
| starch | 0.096 g. |
| precipitated silica | 0.022 g. |
| magnesium stearate | 0.003 g. |

We claim:
1. An isoindoline derivative of the formula:

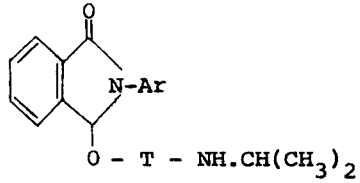

Ar is phenyl and T is alkylene of 2 through 6 carbon atoms, and non-toxic pharmaceutically-acceptable acid addition salts thereof.

2. 3-(2-Isopropylaminoethoxy)-2-phenyl-isoindolin-1-one and non-toxic pharmaceutically-acceptable acid addition salts thereof.

3. 3-(4-Isopropylaminobutoxy)-2-phenyl-isoindolin-1-one and non-toxic pharmaceutically-acceptable acid addition salts thereof.

4. 3-(5-Isopropylaminopentyloxy)-2-phenyl-isoindolin-1-one and non-toxic pharmaceutically-acceptable acid addition salts thereof.

5. 3-(3-Isopropylaminopropoxy)-2-phenyl-isoindolin-1-one and non-toxic pharmaceutically-acceptable acid addition salts thereof.

6. 3-(3-Isopropylamino-2-methylpropoxy)-2-phenyl-isoindolin-1-one and non-toxic pharmaceutically-acceptable acid addition salts thereof.

* * * * *